United States Patent
Oshio et al.

(10) Patent No.: US 12,339,238 B2
(45) Date of Patent: Jun. 24, 2025

(54) INSPECTION DEVICE AND INSPECTION METHOD

(71) Applicant: Panasonic Intellectual Property Management Co., Ltd., Osaka (JP)

(72) Inventors: Shozo Oshio, Osaka (JP); Mitsuru Nitta, Kyoto (JP); Ryosuke Shigitani, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 56 days.

(21) Appl. No.: 18/275,945

(22) PCT Filed: Feb. 1, 2022

(86) PCT No.: PCT/JP2022/003778
§ 371 (c)(1),
(2) Date: Aug. 4, 2023

(87) PCT Pub. No.: WO2022/176596
PCT Pub. Date: Aug. 25, 2022

(65) Prior Publication Data
US 2024/0118220 A1    Apr. 11, 2024

(30) Foreign Application Priority Data

Feb. 22, 2021  (JP) .................. 2021-026793

(51) Int. Cl.
*G01N 21/94* (2006.01)
*G01N 21/25* (2006.01)
(Continued)

(52) U.S. Cl.
CPC ........... *G01N 21/94* (2013.01); *G01N 21/359* (2013.01); *G01N 21/64* (2013.01);
(Continued)

(58) Field of Classification Search
CPC ...... G01N 21/94; G01N 21/359; G01N 21/64; G01N 21/8806; G01N 33/02;
(Continued)

(56) References Cited

U.S. PATENT DOCUMENTS

2014/0248678 A1* 9/2014 Nigola ............... H10H 20/8512
257/89
2014/0339499 A1 11/2014 Tu et al.
(Continued)

FOREIGN PATENT DOCUMENTS

CN 20200135111073644 A  4/2020
JP       4220285 B2      2/2009
(Continued)

OTHER PUBLICATIONS

Chen et al.; Distorted octahedral site occupation-induced high-efficiency broadband near-infrared emission in LiScGe2O6:Cr3+ phosphor ; J. Mater. Chem. C, 2021, 9, 13640 (Year: 2021).*
(Continued)

*Primary Examiner* — Tarifur R Chowdhury
*Assistant Examiner* — Kaitlyn E Kidwell
(74) *Attorney, Agent, or Firm* — Renner, Otto, Boisselle & Sklar, LLP

(57) ABSTRACT

Provided is an inspection device including: a light source including a phosphor; and a photodetector, and detecting, using the photodetector, reflected light of the inspection light reflected by the inspection object. A spectral distribution of the inspection light has at least one maximum value derived from fluorescence emitted by the phosphor, and the maximum value is within a wavelength range of 600 nm or more and 750 nm or less. When Pmax is set as a spectral intensity at the maximum value where the spectral intensity is largest at the at least one maximum value, a largest value of the spectral intensity in a wavelength range longer than 750 nm (Continued)

is 20% or more of Pmax and less than Pmax, and the spectral intensity within a wavelength range of 500 nm or more and 550 nm or less is less than 20% of Pmax.

15 Claims, 4 Drawing Sheets

(51) Int. Cl.
| | |
|---|---|
| *G01N 21/31* | (2006.01) |
| *G01N 21/359* | (2014.01) |
| *G01N 21/64* | (2006.01) |
| *G01N 21/84* | (2006.01) |
| *G01N 21/88* | (2006.01) |
| *G01N 33/02* | (2006.01) |
| *H10H 20/851* | (2025.01) |

(52) U.S. Cl.
CPC ......... *G01N 21/8806* (2013.01); *G01N 33/02* (2013.01); *G01N 21/255* (2013.01); *G01N 21/31* (2013.01); *G01N 21/3151* (2013.01); *G01N 2021/3155* (2013.01); *G01N 2021/3181* (2013.01); *G01N 21/84* (2013.01); *G01N 2201/06193* (2013.01); *H10H 20/851* (2025.01)

(58) Field of Classification Search
CPC ... G01N 2021/3155; G01N 2021/3181; G01N 21/255; G01N 21/3151; G01N 21/31; G01N 2201/06193; G01N 21/84; H01L 33/50
See application file for complete search history.

(56) References Cited

U.S. PATENT DOCUMENTS

| | | | |
|---|---|---|---|
| 2020/0135986 A1 | 4/2020 | Kusano et al. | |
| 2022/0192477 A1* | 6/2022 | Abe | ................... H10H 20/8513 |
| 2022/0233063 A1 | 7/2022 | Abe | |

FOREIGN PATENT DOCUMENTS

| | | | | | |
|---|---|---|---|---|---|
| JP | 2009-161576 A | | 7/2009 | | |
| JP | 2014-44070 A | | 3/2014 | | |
| JP | 2014-160013 A | | 9/2014 | | |
| JP | 2016-3903 A | | 1/2016 | | |
| JP | 2019100925 A | * | 6/2019 | ............. | G01N 21/17 |
| JP | 2020188044 A | * | 11/2020 | ............. | H01L 33/50 |
| WO | 2019/004119 A1 | | 1/2019 | | |
| WO | 2020/235369 A1 | | 11/2020 | | |

OTHER PUBLICATIONS

Kuo et al.; "High color rendering white light-emitting-diode illuminator using the red-emitting Eu2+-activated CaZnOS phosphors excited by blue LED," Opt. Express 18, 8187-8192 (2010) (Year: 2010).*

International Search Report for corresponding Application No. PCT/JP2022/003778, mailed Apr. 19, 2022.

Written Opinion for corresponding Application No. PCT/JP2022/003778, mailed Apr. 19, 2022.

Extended European Search Report for corresponding EP Application No. 22755917.6 dated Jul. 26, 2024.

* cited by examiner

INSPECTION DEVICE AND INSPECTION METHOD

TECHNICAL FIELD

The present invention relates to an inspection device and an inspection method.

BACKGROUND ART

There are known inspection devices and inspection methods for inspecting foreign matter using white light and near-infrared light. Patent Literature 1 discloses a detection method for detecting foreign matter contained in food such as fruits. Specifically, first, absorption spectra of visible light and near-infrared light of reflected light obtained by irradiating food and foreign matter with light are measured, the absorption spectra are subjected to a second derivative process, and a wavelength band exhibiting a different second derivative spectrum between the food and the foreign matter is selected. A second derivative spectroscopic image in the selected wavelength band is then generated for the food. With this, the foreign matter contained in the food is detected.

Patent Literature 2 discloses a food inspection device for identifying the presence or absence of foreign matter in food and its location. Specifically, there is disclosed a device including a surface light source for irradiating food with first and second inspection light having a central wavelength in the near-infrared region, an imaging mechanism for outputting first and second images taken with the first and second inspection light, and a differential image generation unit for generating a differential image of the first and second images. Note that the food inspection device in Patent Literature 2 uses two types of superluminescent diodes (SLD) having different wavelengths without using a phosphor as a light source.

CITATION LIST

Patent Literature

Patent Literature 1: Japanese Patent No. 4220285
Patent Literature 2: Japanese Unexamined Patent Application Publication No. 2014-44070

SUMMARY OF INVENTION

However, the detection method in Patent Literature 1 uses white light having optical components over a wide wavelength range from short-wavelength visible to near-infrared, and thus the efficiency of light utilization is low. In addition, the device used in this detection method needs to emit white light having optical components over a wide wavelength range, and this makes it difficult to make the light source compact and high power. Furthermore, the inspection device of Patent Literature 2 uses optical components biased in the near-infrared region, and thus it was difficult to detect with high sensitivity foreign matter whose light absorption property and light reflection property in the near-infrared region are similar to those of an inspection object.

The present invention has been made in consideration of such issues as described above, which are inherent in related art. An object of the present invention is to provide an inspection device and an inspection method that are capable of detecting foreign matter whose light absorption property and light reflection property in the near-infrared region are similar to those of an inspection object, and are advantageous in making a light source compact and high power.

In response to the above issues, an inspection device according to a first aspect of the present invention includes: a light source including a phosphor; and a photodetector, and detects, using the photodetector, after an inspection object is irradiated with inspection light emitted by the light source, reflected light of the inspection light reflected by the inspection object. A spectral distribution of the inspection light has at least one maximum value derived from fluorescence emitted by the phosphor, and the maximum value is within a wavelength range of 600 nm or more and 750 nm or less. When Pmax is set as a spectral intensity at the maximum value where the spectral intensity is largest in the at least one maximum value, a largest value of the spectral intensity in a wavelength range longer than 750 nm is 20% or more of Pmax and less than Pmax, and the spectral intensity within a wavelength range of 500 nm or more and 550 nm or less is less than 20% of Pmax.

An inspection method according to a second aspect of the present invention includes: irradiating an inspection object with inspection light; and detecting reflected light of the inspection light reflected by the inspection object. A spectral distribution of the inspection light has at least one maximum value derived from fluorescence, and the maximum value is within a wavelength range of 600 nm or more and 750 nm or less. When Pmax is set as a spectral intensity at the maximum value where the spectral intensity is largest in the at least one maximum value, a largest value of the spectral intensity in a wavelength range longer than 750 nm is 20% or more of Pmax and less than Pmax, and the spectral intensity within a wavelength range of 500 nm or more and 550 nm or less is less than 20% of Pmax.

DESCRIPTION OF EMBODIMENTS

Figure 1:
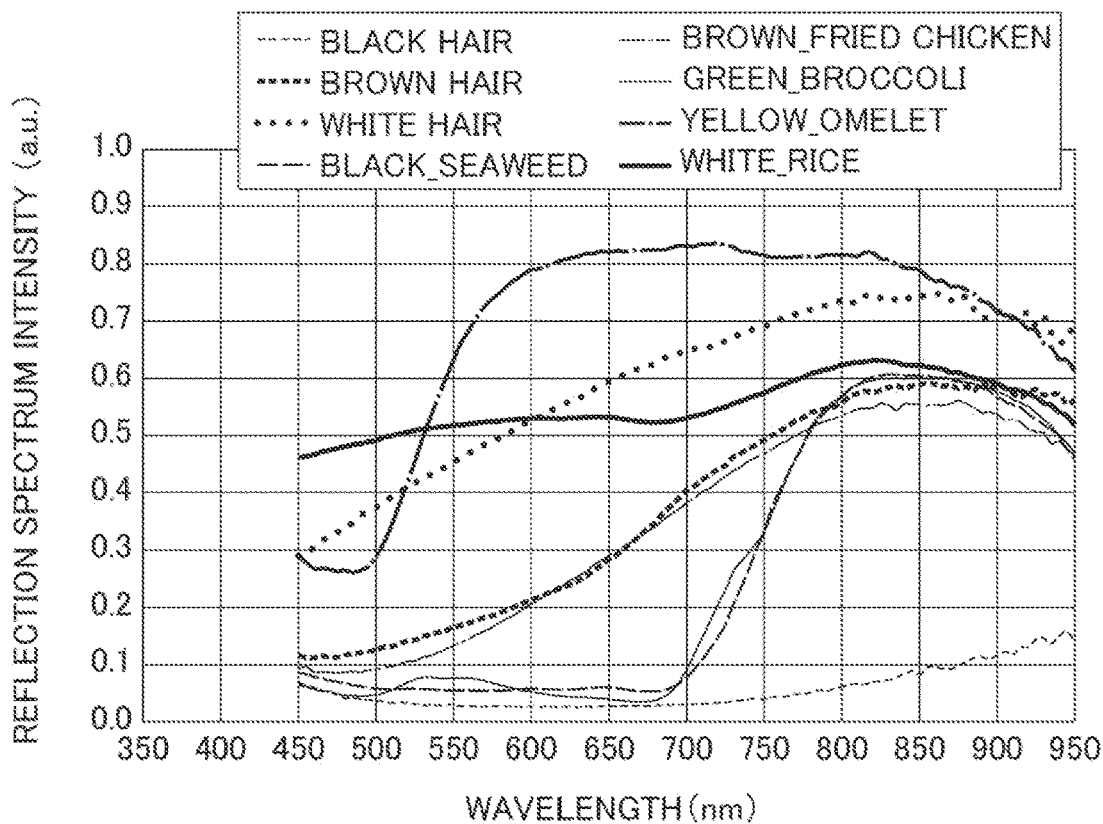
FIG. 1 is a graph illustrating a relationship between the intensity and the wavelength in reflection spectra of inspection objects and foreign matter.

Referring to the drawings, a description is given below of an inspection device and an inspection method according to the present embodiment. Note that dimensional ratios in the drawings are exaggerated for convenience of the description and are sometimes different from actual ratios.

[Principle of Inspection Device and Inspection Method]

The present inventors mixed foreign matter into an inspection object, then irradiated the inspection object with light while changing the spectral distribution of the irradiation light, and thus investigated how foreign matter in the inspection object was detected using a photodetector. Specifically, a box meal was selected as the inspection object, and some hairs of different tones were mixed as the foreign matter. While the box meal was irradiated with light, the spectral distribution of the irradiation light was changed, and the ingredients and hairs in the box meal were captured with a photodetector. Consequently, it was found that when light having a specific spectral distribution was used, the foreign matter could be detected with high sensitivity and with good reproducibility regardless of the color of the foreign matter.

As a result of investigating the reason why foreign matter could be detected in this way, it was found that the appearance of the foreign matter through the photodetector (imaging element) was related to a light reflection property of the inspection object and foreign matter. In addition, it was found that good detection results can be obtained when, in the irradiation light, the intensity of red light is strong, near-infrared light is included in no small amount, and the spectral distribution is broad.

FIG. 1 illustrates the results of investigating wavelength dependency of reflectance regarding hairs having different tones and ingredients in a typical box meal. Seaweed, fried chicken, broccoli, an omelet, and rice were used as ingredients in the box meal. Black, brown, and white hairs were used as hairs.

As illustrated in FIG. 1, it can be seen that the reflectance decreases in many ingredients having dark tones such as seaweed, broccoli, and fried chicken as the wavelength becomes shorter from the near-infrared region to the red light region. It can also be seen that the reflectance also decreases in black hair and brown hair as the wavelength becomes shorter from the near-infrared region. However, it can be seen that the reflectance hardly decreases in an omelet, rice, and white hair even when the wavelength becomes shorter from the near-infrared region to the red light region.

That is, it can be seen that the wavelength dependence of reflection spectra of the ingredients and hair has a large degree of different behavior within a wavelength range of 550 nm or more and 750 nm or less, especially within a wavelength range of 600 nm or more and 700 nm or less. Specifically, seaweed, broccoli, and black hair exhibit a large decrease in the reflectance within said wavelength ranges, while fried chicken and brown hair exhibit a smaller decrease in the reflectance than that of seaweed, broccoli, and black hair. In contrast, fried egg, rice, and white hair do not exhibit a significant decrease in the reflectance even within said wavelength ranges. Therefore, it can be seen that foreign matter can be detected by utilizing the difference in the red light reflectance. For example, when black or brown hair is mixed on the surface of rice and an omelet, the black or brown hair can be detected by performing irradiation with red light, detecting the reflected light, and utilizing the difference in reflectances.

However, when the intensity of red light contained in irradiation light is small, even when the reflected light is detected using a photodetector, the S/N (signal/noise ratio) deteriorates, and the red light cannot be detected with high precision. Therefore, by irradiating an inspection object with strong red light, the signal intensity of red light detected using an photodetector is increased and the S/N is improved, and this clarifies the difference in signal intensities between the inspection object and the foreign matter.

As described above, there are many combinations in which the wavelength dependence of reflection spectra of ingredients in a box meal and hair has a large degree of different behavior in a wavelength range of 550 nm or more and 750 nm or less, especially within a wavelength range of 600 nm or more and 700 nm or less. Therefore, when the optical component intensity within these wavelength ranges is large, this is considered to work effectively in detecting hair as foreign matter.

Here, as illustrated in FIG. 1, since seaweed, broccoli, and black hair have dark tones, the behavior of reflected light is almost the same within the wavelength range of 600 nm or more and 700 nm or less. Therefore, when red light is used as irradiation light, it is difficult to detect black hair when the black hair is mixed on the surface of seaweed and broccoli.

However, black hair easily absorbs near-infrared light and has the property of hardly reflecting. That is, comparing the reflectances of black hair and the ingredients of a box meal, almost all the ingredients exhibit relatively high reflectances of about 50% or more at least within a wavelength range of 750 nm or more and 900 nm or less, while the reflectance of black hair is less than 20%, and this is a large difference. Therefore, it can be seen that black hair in the ingredients can be detected with high sensitivity using the reflected light of near-infrared light.

Here, as illustrated in FIG. 1, the reflectances of brown hair and white hair within a wavelength range of 750 nm or more and 900 nm or less are similar to those of the ingredients. Thus, it is difficult to detect brown hair and white hair in ingredients using near-infrared light. However, as described above, the reflectances of brown hair and white hair within a wavelength range of 550 nm or more and 750 nm or less have some differences with respect to the reflectances of ingredients. Therefore, brown hair and white hair in the ingredients can be detected with high sensitivity using the reflected light of red light.

Thus, strong red light is effective in detecting brown hair and white hair and improving the signal/noise ratio, and near-infrared light is effective in detecting black hair. Thus, by using light containing a near-infrared optical component and a strong red optical component as inspection light, it becomes possible to detect foreign matter with high sensitivity regardless of tones.

The inspection device and inspection method according to the present embodiment are based on such knowledge, and are characterized by using light that is particularly favorable for detecting hair mixed in the ingredients of a box meal. Note that it is possible to apply the inspection device and inspection method according to the present embodiment to purposes other than the detection of hair mixed in the ingredients of a box meal. That is, considering that both the ingredients and the hair can be viewed as organic matter and that the ingredients can be viewed as food and the hair as not food, the inspection device and inspection method can be applied to the detection of other organic foreign matter contained in specific organic matter and the detection of organic foreign matter contained in food and luxury items. Therefore, the inspection device and inspection method according to the present embodiment are not limited to the inspection of hair contained in the ingredients of a box meal and can be used for other inspections.

[Configuration of Inspection Device]

Figure 2:
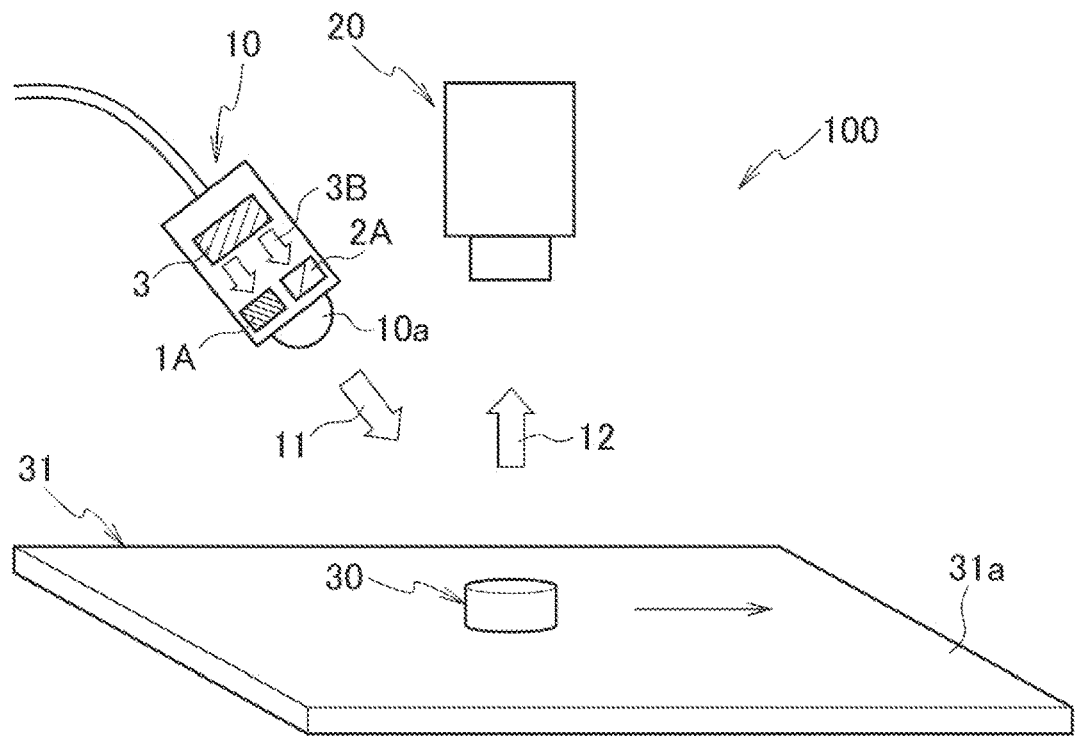
FIG. 2 is a schematic diagram illustrating a configuration of an inspection device according to the present embodiment.

FIG. 2 schematically illustrates a configuration of the inspection device according to the present embodiment. An inspection device 100 according to the present embodiment at least includes a light source 10 including a phosphor, and a photodetector 20. After an inspection object 30 is irradiated with inspection light 11 emitted by the light source 10, the photodetector 20 detects reflected light 12 of the inspection light 11 reflected by the inspection object 30.

Figure 3:
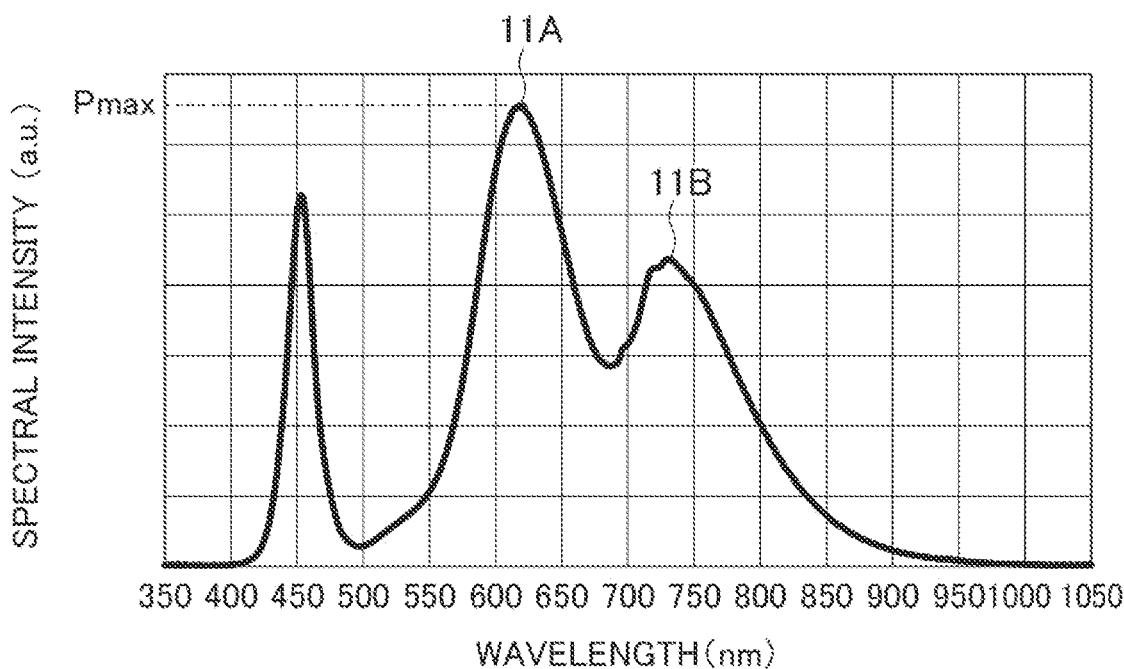
FIG. 3 is a graph illustrating an example of a spectral distribution of inspection light emitted by a light source of the inspection device according to the present embodiment.
Figure 4:
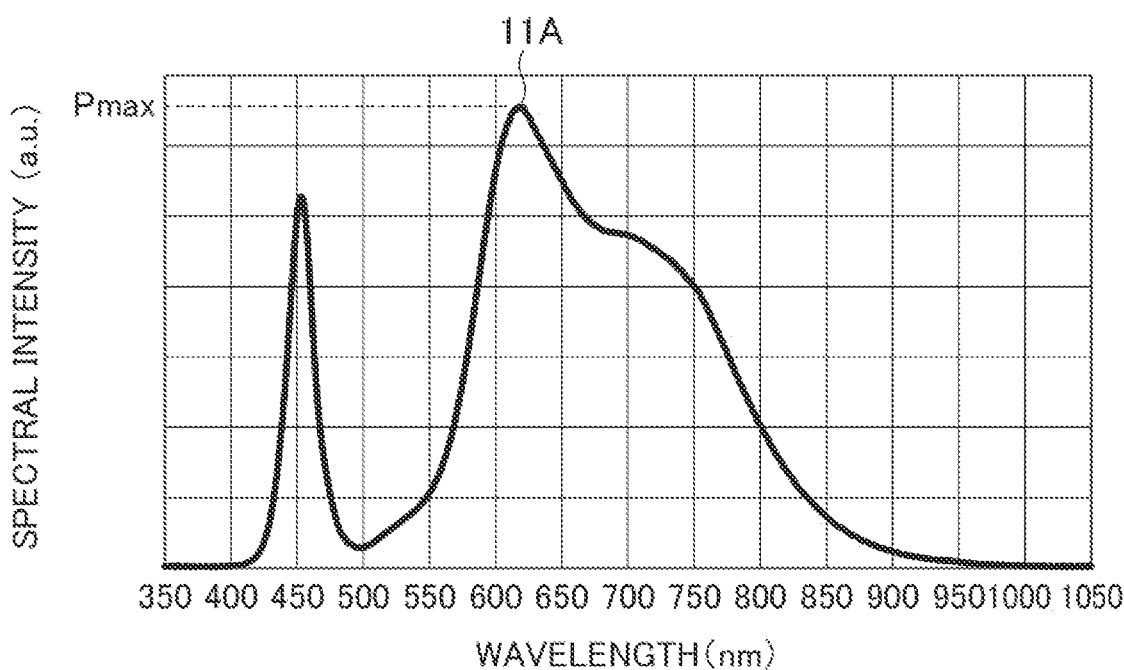
FIG. 4 is a graph illustrating another example of the spectral distribution of the inspection light emitted by the light source of the inspection device according to the present embodiment.

In such an inspection device 100, the inspection light 11 emitted by the light source 10 has a spectral distribution illustrated in, for example, FIG. 3 or FIG. 4. Specifically, the spectral distribution of the inspection light 11 has at least one maximum value 11A, 11B derived from fluorescence emitted by the phosphor. At least the maximum value 11A is preferably within a wavelength range of 600 nm or more and 750 nm or less, more preferably within a wavelength range of 610 nm or more and 700 nm or less, even more preferably within a wavelength range of 620 nm or more and 680 nm or less.

When Pmax is set as the spectral intensity at the maximum value 11A where the spectral intensity is largest at the at least one maximum value 11A, 11B, a largest value of the spectral intensity in a wavelength range longer than 750 nm is preferably 20% or more of Pmax and less than Pmax. The largest value of the spectral intensity in the wavelength range longer than 750 nm is more preferably 30% or more of Pmax and less than 80% of Pmax, even more preferably 50% or more of Pmax and less than 70% of Pmax. The spectral intensity in a wavelength range from 500 nm or more and 550 nm or less is preferably less than 20% of Pmax, more preferably less than 18% of Pmax, even more preferably less than 16% of Pmax.

As described above, by using light containing a near-infrared optical component and a strong red optical component as the inspection light 11, foreign matter can be detected with high sensitivity. Then, as illustrated in FIGS. 3 and 4, the inspection light 11 contains red light having a maximum value in a wavelength range of 600 nm or more and 750 nm or less and near-infrared light having a wavelength range longer than 750 nm. In addition, the spectral intensity of the red light is larger than that of the near-infrared light. As described above, light containing both the red and near-infrared optical components having a wavelength difference is used as the inspection light 11, and thus even similar kinds of foreign matter (for example, hairs of different tones) that are difficult to detect only using near-infrared light can be detected using red light. Therefore, the detection probability of foreign matter increases, and it becomes possible to enhance the inspection precision. Furthermore, an inspection object 30 is irradiated with light having a strong intensity of red light together with near-infrared light, and thus this enhances the inspection precision of an inspection object and foreign matter having a smaller reflectance in the red wavelength range than in the near-infrared range.

Moreover, the spectral intensity of the inspection light 11 within a wavelength range of 500 nm or more and 550 nm or less is less than 20% of Pmax. That is, in the inspection light 11, the intensity of red light is increased, but the intensity of green light is reduced. Thus, since optical components are concentrated in a specific wavelength range for determining the quality of inspection, the light utilization efficiency, and the electro-optical conversion efficiency of the light source 10 can be enhanced. Consequently, the inspection device 100 has advantages in reduction in size and having high output, and in having high efficiency.

Thus, the inspection device 100 can detect similar kinds of foreign matter, which are difficult to detect only using near-infrared light, with high precision by using both the near-infrared light and the red light, and further, the device can be made compact.

In the spectral distribution of the inspection device 100, it is preferable that the number of maximum values 11A and 11B within a wavelength range of 500 nm or more and 1000 nm or less be 1 or 2. Furthermore, it is more preferable that the number of maximum values 11A and 11B within a wavelength range of 600 nm or more and 900 nm or less be 1 or 2. It is also preferable that the maximum value 11A derived from the fluorescent component emitted by the phosphor takes the largest intensity value of the spectral distribution. In this way, the inspection light 11 is made to be light in which optical components are concentrated in the red-to-near-infrared wavelength range for determining the quality of inspection. Therefore, light source design with a high electro-optical conversion efficiency is facilitated and also inspection light 11 having a high utilization efficiency is obtained, and thus this is advantageous for reduction in size and high output of the light source 10 and for making the inspection device 100 compact.

Regarding the spectral distribution of the inspection device 100, it is preferable that the amount of change with respect to wavelength be less than 5% per 1 nm wavelength for the spectral intensity within a wavelength range of 550 nm or more and 850 nm or less. It is more preferable that the amount of change with respect to wavelength be less than 5% per 1 nm wavelength for the spectral intensity within a wavelength range of 550 nm or more and 950 nm or less. By making a spectral distribution derived from the fluorescent component emitted by the phosphor wider, the intensity change with respect to wavelength is small, and furthermore, the inspection light has optical components in all the wavelength ranges mentioned above. Therefore, it becomes possible to inspect the inspection object 30 with relatively high precision even when the wavelength dependence of the light reflection property or the wavelength dependence of the light absorption property is large.

(Light Source)

The light source 10 of the inspection device 100 is preferably a combination of a solid-state light emitting element 3 and a phosphor. A wavelength conversion-type light emitting element combining a solid-state light emitting element 3 and a phosphor is an all-solid-state light source that has a long life and excellent reliability and further facilitates circuit design. By utilizing such a wavelength conversion-type light emitting element, it becomes possible to reduce the burden of inspection and maintenance of the light source over a long period of time.

Figure 5:
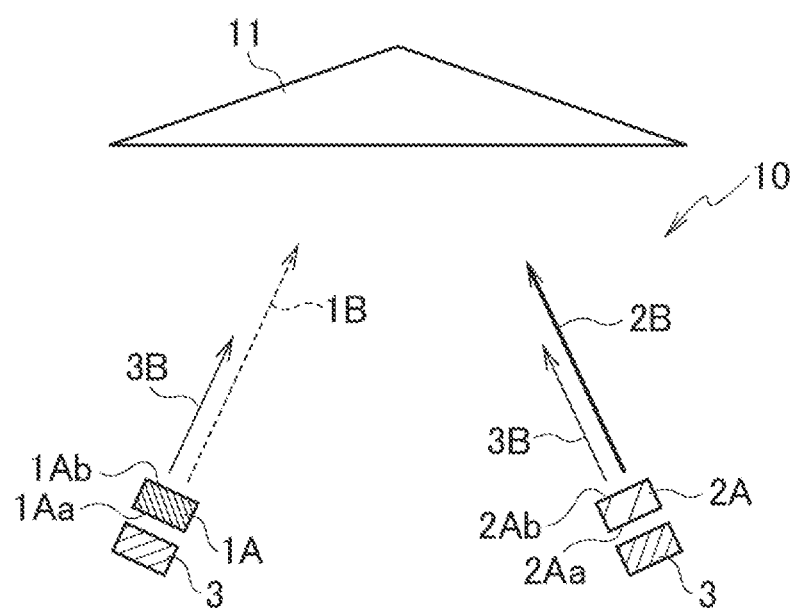
FIG. 5 is a schematic diagram illustrating an example of the configuration of the light source in the inspection device according to the present embodiment.

In more detail, as illustrated in FIGS. 2 and 5, the light source 10 includes the solid-state light emitting element 3, a first wavelength converter 1A including a red phosphor that emits first wavelength-converted light 1B, and a second wavelength converter 2A including a near-infrared phosphor that emits second wavelength-converted light 2B. The solid-state light emitting element 3 emits primary light 3B. The first wavelength converter 1A absorbs at least part of the primary light 3B and converts it into the first wavelength-converted light 1B, which mainly contains a red optical component. The second wavelength converter 2A absorbs part of the primary light 3B and converts it into the second wavelength-converted light 2B, which mainly contains a near-infrared optical component.

Specifically, the first wavelength converter 1A receives primary light 3B at a front surface 1Aa and emits the primary light 3B and first wavelength-converted light 1B from a back surface 1A*b*. Furthermore, the second wavelength converter 2A receives primary light 3B at a front surface 2A*a* and emits the primary light 3B and second wavelength-converted light 2B at a back surface 2A*b*. Then, mixed light (inspection light 11) of the first wavelength-converted light 1B, the second wavelength-converted light 2B, and the primary light 3B is output from an output surface 10*a* of the light source 10.

As illustrated in FIG. 2, the light source 10 can have a configuration in which the first wavelength converter 1A and the second wavelength converter 2A are arranged in parallel along the light output surface of one solid-state light emitting element 3. As illustrated in FIG. 5, the light source 10 can also have a configuration in which a first wavelength conversion-type light emitting element combining the solid-state light emitting element 3 and the first wavelength converter 1A, and a second wavelength conversion-type light emitting element combining the solid-state light emitting element 3 and the second wavelength converter 2A are arranged in parallel.

The light source 10 can also have a configuration in which the solid-state light emitting element 3 and a stacked body of multiple wavelength converters are combined. Here, the stacked body can have a configuration in which the first wavelength converter 1A containing a red phosphor and the second wavelength converter 2A containing a near-infrared phosphor are stacked. The first wavelength converter 1A absorbs at least part of primary light 3B and converts it into the first wavelength-converted light 1B. The second wavelength converter 2A also absorbs at least part of primary light 3B and converts it into the second wavelength-converted light 2B. The stacked body receives primary light 3B at the front surface and emits the primary light 3B, the first wavelength-converted light 1B, and the second wavelength-converted light 2B from the back surface. Note that the second wavelength converter 2A can also be made to exclusively absorb the first wavelength-converted light 1B emitted by the first wavelength converter 1A to emit the second wavelength-converted light 2B.

Note that the light source 10 can be configured by combining the solid-state light emitting element 3 with a single wavelength converter, and said wavelength converter can be configured to include both a red phosphor and a near-infrared phosphor. In this case, the wavelength converter absorbs at least part of primary light 3B and converts it into first wavelength-converted light 1B and second wavelength-converted light 2B. The wavelength converter receives primary light 3B at the front surface and emits the primary light 3B, the first wavelength-converted light 1B, and the second wavelength-converted light 2B from the back surface.

<Solid-State Light Emitting Element>

In the light source 10, the solid-state light emitting element 3 preferably emits light having a largest intensity value within a wavelength range of 440 nm or more and less than 480 nm. Specifically, the solid-state light emitting element 3 is preferably a blue light emitting element that emits light having a largest intensity value within a wavelength range of 440 nm or more and less than 480 nm, especially 445 nm or more and less than 470 nm. With such a configuration, the light emitted by the solid-state light emitting element 3 has a shorter wavelength than the maximum value formed due to the fluorescent component emitted by the phosphor. Thus, by irradiating a phosphor with blue light emitted by the solid-state light emitting element 3, red and near-infrared optical components can be easily obtained as wavelength-converted light of the phosphor. Moreover, since the solid-state light emitting element 3 emitting blue light is to obtain, the inspection device 100 can be made advantageous for industrial production.

The solid-state light emitting element 3 is preferably a light emitting diode or a laser diode. In addition, by using an LED module or a laser diode emitting high energy light of 1 W or more as the solid-state light emitting element 3, the inspection device 100 can expect an optical output containing a near-infrared optical component of a several hundred mW class. By using an LED module emitting light of 3 W or more or 10 W or more as the solid-state light emitting element 3, the inspection device 100 can expect an optical output of a several W class. By using an LED module emitting light of 30 W or more as the solid-state light emitting element 3, the inspection device 100 can expect an optical output of more than 10 W. By using an LED module emitting light of 100 W or more as the solid-state light emitting element 3, the inspection device 100 can expect an optical output of more than 30 W. Note that as the laser diode, for example, an edge emitting laser (EEL), a vertical cavity surface emitting laser (VCSEL), and the like can be used.

There are preferably multiple solid-state light emitting elements 3. This can increase the output of primary light 3B, resulting in an inspection device advantageous for increasing the output. Note that the number of solid-state light emitting elements is not particularly limited, but it can be, for example, 9 or more, 16 or more, 25 or more, 36 or more, 49 or more, 64 or more, 81 or more, or 100 or more. In addition, the upper limit of the number of solid-state light emitting elements is not particularly limited, but for example, it can be 9, 16, 25, 36, 49, 64, 81, or 100.

In the inspection device 100, the solid-state light emitting element 3 is preferably a surface emitting light source of a surface emitting type. This suppresses variation in intensity distribution and unevenness in the tone of the primary light 3B, and thus the inspection device is made advantageous in suppressing unevenness in the intensity of the output light.

The light energy density of the primary light 3B emitted by the solid-state light emitting element 3 is preferably over 0.3 W/mm$^2$, more preferably over 1.0 W/mm$^2$. In this way, the light energy density of the primary light 3B is large, and thus with a configuration in which the first wavelength converter 1A and the second wavelength converter 2A are irradiated with primary light 3B that is diffused, relatively intense inspection light 11 can be emitted. With a configuration in which the first wavelength converter 1A and the second wavelength converter 2A are directly irradiated with primary light 3B that is not diffused, inspection light 11 having a large light energy density can be emitted. Note that the upper limit of the light energy density of the primary light 3B emitted by the solid-state light emitting element 3 is not particularly limited and can be 30 W/mm$^2$, for example.

<First Wavelength Converter>

The first wavelength converter 1A can be a wavelength converter in which a red phosphor is sealed with a silicone resin. Also, the first wavelength converter 1A can be an all-inorganic wavelength converter in which a red phosphor is sealed with a low-melting-point glass. Furthermore, the first wavelength converter 1A can also be an all-inorganic wavelength converter made from mainly a red phosphor using a binder or the like. The first wavelength converter 1A can also be a sintered body obtained by sintering a red phosphor, that is, can be fluorescent ceramic.

The thickness of the first wavelength converter 1A is not particularly limited, but the largest thickness is preferably 100 µm or more and less than 5 mm, more preferably 200 µm or more and less than 1 mm.

The first wavelength converter 1A preferably has translucency. With this, primary light 3B and optical components that are wavelength-converted inside the wavelength converter can be transmitted through the first wavelength converter 1A to be emitted therefrom.

The red phosphor contained in the first wavelength converter 1A is a phosphor that absorbs primary light 3B and converts it into first wavelength-converted light 1B. The red phosphor preferably emits red light having a largest intensity value within a wavelength range of 600 nm or more and less than 660 nm, more preferably emits red light having a largest intensity value within a wavelength range of 610 nm or more and less than 650 nm. In this way, the primary light 3B emitted by the solid-state light emitting element 3 can be easily wavelength-converted to a red optical component, and thus this is advantageous for obtaining the red optical component required for the inspection light 11.

As the red phosphor, a phosphor that is activated with at least one of a rare earth ion or a transition metal ion and emits red light can be used. The rare earth ion is preferably at least one of $Ce^{3+}$ or $Eu^{2+}$. The transition metal ion is preferably $Mn^{4+}$. The red phosphor is preferably an oxide, sulfide, nitride, halide, oxysulfide, oxynitride, or oxyhalide containing a fluorescent ion mentioned above.

The red phosphor is more preferably an oxide, sulfide, nitride, halide, oxysulfide, oxynitride, or oxyhalide containing $Eu^{2+}$ as a light emission center. The red phosphor is preferably a phosphor made from a metal composite nitride or metal composite oxynitride activated with $Eu^{2+}$. Examples of such an $Eu^{2+}$ activated nitride-based phosphor include phosphors of alkaline earth metal nitride silicate, alkaline earth metal nitride aluminosilicate, alkaline earth metal oxynitride silicate, and alkaline earth metal oxynitride aluminosilicate. Examples of the $Eu^{2+}$ activated nitride-based phosphor include $MAlSiN_3:Eu^{2+}$, $M_2Si_5N_8:Eu^{2+}$, and $MAlSi_4N_7:Eu^{2+}$. Note that M is constituted by at least one element selected from the group consisting of Ca, Sr, and Ba. Furthermore, an example of the $Eu^{2+}$ activated nitride-based phosphor is a phosphor in which part of an $Si^{4+}$—$N^{3+}$ combination in a crystal constituting a compound mentioned above is replaced with $Al^{3+}$—$O^{2-}$.

A red phosphor having $Eu^{2+}$ as a light emission center can absorb blue light and convert it into red light having a broad spectral distribution. Such a red phosphor is being improved with the development of light emitting diode (LED) technology. A red phosphor that can convert absorbed blue light with a photon conversion efficiency close to the theoretical limit is commercially available for LED lighting, and thus procurement thereof is easy. Thus, the use of such a red phosphor not only reduces the primary light 3B emitted by the solid-state light emitting element 3, but also makes it possible to easily obtain red light having the wide spectral distribution required for inspection.

<Second Wavelength Converter>

The second wavelength converter 2A can be a wavelength converter in which a near-infrared phosphor is sealed with a silicone resin. Also, the second wavelength converter 2A can be an all-inorganic wavelength converter in which a near-infrared phosphor is sealed with a low-melting-point glass. Furthermore, the second wavelength converter 2A can also be an all-inorganic wavelength converter made from mainly a near-infrared phosphor using a binder or the like. The second wavelength converter 2A can also be a sintered body obtained by sintering a near-infrared phosphor, that is, can be fluorescent ceramic. Note that since the shape of the second wavelength converter 2A is the same as that of the first wavelength converter 1A, overlapping descriptions thereof are omitted.

The second wavelength converter 2A preferably has translucency. With this, in addition to the primary light 3B, optical components that are wavelength-converted inside the wavelength converter can also be transmitted through the second wavelength converter 2A to be emitted therefrom. Also, the second wavelength converter 2A preferably transmits light having a wavelength of 750 nm. Consequently, the second wavelength converter 2A transmits near-infrared light, and thus photons inside the wavelength converter being absorbed by the wavelength converter itself and disappearing is suppressed.

The near-infrared phosphor contained in the second wavelength converter 2A is a phosphor that absorbs primary light 3B and converts it into second wavelength-converted light 2B. The near-infrared phosphor preferably emits near-infrared light having a largest intensity value within a wavelength range of 700 nm or more and less than 1000 nm, more preferably emits near-infrared light having a largest intensity value within a wavelength range of 720 nm or more and less than 900 nm. In this way, the primary light 3B emitted by the solid-state light emitting element 3 can be easily wavelength-converted to a near-infrared optical component, and thus this is advantageous for obtaining the near-infrared optical component required for the inspection light 11.

As the near-infrared phosphor, for example, various inorganic phosphors known as near-infrared light sources can be used. Specifically, as the near-infrared phosphor, a phosphor that is activated with at least one of a rare earth ion or a transition metal ion and emits fluorescence containing a near-infrared optical component can be used. The rare earth ion is preferably at least one selected from the group consisting of $Nd^{3+}$, $Eu^{2+}$, $Ho^{3+}$, $Er^{3+}$, $Tm^{3+}$, and $Yb^{3+}$. The transition metal ion is preferably at least one selected from the group consisting of $Ti^{3+}$, $V^{4+}$, $Cr^{3+}$, $V^{3+}$, $Cr^{3+}$, $V^{2+}$, $Mn^{4+}$, $Fe^{3+}$, $Co^{3+}$, $Co^{2+}$, and $Ni^{2-}$. The near-infrared phosphor is preferably an oxide, sulfide, nitride, halide, oxysulfide, oxynitride, or oxyhalide containing a fluorescent ion mentioned above.

In the near-infrared phosphor, a preferable fluorescent ion is $Cr^{3+}$. The use of $Cr^{3+}$ as a fluorescent ion makes it easier to obtain a near-infrared phosphor that absorbs visible light, especially blue or red light, and converts it into a near-infrared optical component. It also becomes easier depending on the type of host to change the light absorption peak wavelength and the fluorescence peak wavelength, and this is advantageous for changing the excitation spectrum shape and the fluorescence spectrum shape.

The near-infrared phosphor is preferably a phosphor that has many practical applications and has a garnet-type crystal structure. The near-infrared phosphor is preferably a phosphor made from a metal composite oxide activated with $Cr^{3+}$. Specifically, examples of the near-infrared phosphor includes garnet phosphors represented by general formulae $Ln_3B'_2(AlO_4)_3:Cr^{3+}$ and $Ln_3B'_2(GaO_4)_3:Cr^{3+}$. Note that Ln is a rare earth element, and B' is at least one element selected from Al, Ga, or Sc. Ln is preferably at least one element selected from the group consisting of Y, La, Gd, and Lu. Furthermore, an example of the near-infrared phosphor is also a phosphor in which part of an $Ln^{3+}$—$B'^{3+}$ combination in a crystal constituting a garnet phosphor mentioned above is replaced with an $M^{2+}$-$Si^{4+}$ combination. Note that M is an alkaline earth metal and is preferably at least one element selected from the group consisting of Ca, Sr, and Ba. The near-infrared phosphor may be a solid solution of garnet phosphors mentioned above.

The near-infrared phosphor is preferably at least one of a rare-earth aluminum garnet phosphor or a rare-earth gallium garnet phosphor. Specifically, the near-infrared phosphor is preferably at least one selected from the group consisting of: $Y_3Al_2(AlO_4)_3:Cr^{3+}$, $La_3Al_2(AlO_4)_3:Cr^{3+}$, $Gd_3Al_2(AlO_4)_3:Cr^{3+}$, $Y_3Ga_2(AlO_4)_3:Cr^{3+}$, $La_3Ga_2(AlO_4)_3:Cr^{3+}$, $Gd_3Ga_2(AlO_4)_3:Cr^{3+}$, $Y_3Sc_2(AlO_4)_3:Cr^{3+}$, $La_3Sc_2(AlO_4)_3:Cr^{3+}$, $Gd_3Sc_2(AlO_4)_3:Cr^{3+}$, $Y_3Ga_2(GaO_4)_3:Cr^{3+}$, $La_3Ga_2(GaO_4)_3:Cr^{3+}$, $Gd_3Ga_2(GaO_4)_3:Cr^{3+}$, $Y_3Sc_2(GaO_4)_3:Cr^{3+}$, $La_3Sc_2(GaO_4)_3:Cr^{3+}$, and $Gd_3Sc_2(GaO_4)_3:Cr^{3+}$. In addition, the near-infrared phosphor may be a solid solution having a phosphor mentioned above as an end component.

Such a near-infrared phosphor having $Cr^{3+}$ as a light emission center can absorb not only blue light but also red light and convert them to near-infrared light having a wider spectral distribution. Also, such a near-infrared phosphor is capable of converting absorbed light with a photon conversion efficiency close to the theoretical limit. Thus, the use of such a near-infrared phosphor not only reduces the primary light 3B emitted by the solid-state light emitting element 3, but also makes it possible to easily obtain near-infrared light having a wide spectral distribution required for inspection.

(Photodetector)

For the photodetector 20, various detectors can be used as long as they can detect reflected light 12 of inspection light 11 reflected by the inspection object 30. Specifically, quantum type photodetectors that detect the electric charge generated when light enters a PN junction of a semiconductor, such as a photodiode, phototransistor, photoIC, CCD image sensor, and CMOS image sensor, can be used. In addition, thermal type photodetectors that detect the change in electrical properties caused by a temperature rise due to heat generated when light is received, such as thermopiles using the thermoelectric effect and pyroelectric elements using the pyroelectric effect can also be used. Furthermore, infrared films that are sensitive to light can also be used as photodetectors.

As the photodetector 20, a single element using a photoelectric conversion element alone may be used, or an imaging element integrating photoelectric conversion elements may be used. The form of the imaging element may be linear with a one-dimensional arrangement or planar with a two-dimensional arrangement.

A method for inspecting an inspection object 30 using the inspection device 100 having such a configuration will be described. As illustrated in FIG. 2, the inspection object 30 is placed on a surface 31a of a conveyor 31 and moves continuously in the direction of the arrow in the figure. The light source 10 is installed diagonally above the conveyor 31, and the photodetector 20 is installed above the conveyor 31.

In such an inspection device 100, the inspection light 11 is emitted from the light source 10 toward the inspection object 30. On the surface of the inspection object 30 irradiated with the inspection light 11, red light and near-infrared light are reflected according to the light absorption property and the light reflection property of the irradiated object. Then, the reflected light 12 of the inspection light 11 reflected by the inspection object 30 is detected by the photodetector 20.

Here, as described above, when the inspection object 30 is the ingredients of a box meal and foreign matter is hair, brown and gray hair in the ingredients can be detected in the image with red light captured by the photodetector 20, and black hair in the ingredients can be detected in the image with near-infrared light. For example, in the image, the foreign matter can be detected by indicating substances having a high light absorption property in black and indicating substances having a low light absorption property in white.

When it is determined as a result of the inspection that the inspection object 30 contains no foreign matter, the inspection object 30 is moved to undergo post-processing. In contrast, when it is determined as a result of the inspection that the inspection object 30 contains foreign matter, the inspection object 30 is moved to another line, for example, and thus an item in which the foreign matter is mixed can be removed.

In the inspection device 100, the inspection object 30 can be food. Note that "food" is a general term for items that are eaten by humans, such as ingredients in box meals, grains, vegetables, fruits, meat, fish, processed food, and beverages.

As mentioned above, the inspection device 100 inspects whether or not an inspection object contains foreign matter. For example, the inspection device 100 can be used to detect the presence or absence and condition of foreign matter mixed in food. Among other things, the inspection device 100 can detect organic matter, especially hair, as foreign matter.

Here, in food-related factories where work is done by humans, there is a risk that not only foreign matter derived from inorganic matter (metals, inorganic compounds, and the like), which is easily detected by X-rays, but also foreign matter derived from humans, petroleum products, and plants, which is difficult to detect using X-rays, may get into food. However, by using the inspection device 100, foreign matter derived from organic matter can be detected, and thus it becomes possible to reduce the risk of mixture of foreign matter.

The inspection device 100 may further include a selecting means for selecting an inspection object 30 in which foreign matter has been detected. Selecting can be carried out by means such as mechanically moving the inspection object in which foreign matter has been detected (abnormal object) to another line or blowing it away with an air gun. In this way, normal and abnormal inspection objects can be selected, and thus the abnormal objects can be consolidated together. Thus, this is convenient for the work of identifying abnormal conditions and work for normalization.

The inspection device 100 may further include a visualization means for visualizing foreign matter. The visualization of foreign matter can be performed using a known means utilizing, for example, an imaging tube or an imaging element. This allows the human eye to immediately detect the abnormal condition of an inspection object, and thus it becomes possible for a worker to correctly understand the abnormal condition of the inspection object.

The inspection device 100 also preferably includes an integrated means for linking visualized foreign matter to an inspection object. The integration can be carried out by a display means for displaying a composite image obtained by superimposing an image of foreign matter captured by an imaging sensor and an image of an inspection object. This integrates the abnormal object itself and the abnormal information it has (foreign matter information), and thus it becomes possible to see the actual object in front of one's eyes, to correctly understand the abnormal condition it has, and to take appropriate measures. The integration can also be carried out by a means for attaching a tag (mark) to an inspection object that has been found to contain foreign matter. This makes it possible to easily distinguish between normal and abnormal objects from a distance.

Thus, the inspection device 100 according to the present embodiment is an inspection device which includes a light source 10 including a phosphor, and a photodetector 20, and in which after an inspection object 30 is irradiated with inspection light 11 emitted by the light source 10, reflected light 12 of the inspection light 11 reflected by the inspection object 30 is detected using the photodetector 20. The spectral distribution of the inspection light 11 has at least one maximum value 11A, 11B derived from fluorescence emitted by the phosphor, and the maximum values 11A, 11B are within a wavelength range of 600 nm or more and 750 nm or less. Pmax is set as the spectral intensity at the maximum value 11A where the spectral intensity is largest at the at least one maximum value 11A, 11B. In this case, the largest value of the spectral intensity in a wavelength range longer than 750 nm is 20% or more of Pmax and less than Pmax, and the spectral intensity within a wavelength range of 500 nm or more and 550 nm or less is less than 20% of Pmax.

Moreover, an inspection method according to the present embodiment has a step of irradiating an inspection object 30 with inspection light 11 and a step of detecting reflected light 12 of the inspection light 11 reflected by the inspection object 30. The spectral distribution of the inspection light 11 has at least one maximum value 11A, 11B derived from fluorescence, and the maximum values 11A and 11B are within a wavelength range of 600 nm or more and 750 nm or less. Pmax is set as the spectral intensity at the maximum value 1A where the spectral intensity is largest at the at least one maximum value 11A, 11B. In this case, the largest value of the spectral intensity in a wavelength range longer than 750 nm is 20% or more of Pmax and less than Pmax, and the spectral intensity in a wavelength range from 500 nm or more and 550 nm or less is less than 20% of Pmax.

Since the inspection device 100 and the inspection method according to the present embodiment utilize both the red optical component and the near-infrared optical component, it becomes possible to improve the inspection precision for similar kinds of foreign matter that are difficult to detect only by using near-infrared light, such as hairs having different tones. In addition, since optical components are concentrated in the wavelength range for determining the quality of inspection, it becomes possible to enhance the electro-optical conversion efficiency. Furthermore, the inspection object 30 is irradiated with red light having a high intensity together with near-infrared light, and thus it becomes possible to inspect with high precision organic matter-based foreign matter whose reflectance in the red region is smaller than that in the near-infrared region.

Moreover, the phosphor provided in the light source 10 preferably includes a red phosphor that emits red light having a largest intensity value within a wavelength range of 600 nm or more and less than 660 nm and a near-infrared phosphor that emits near-infrared light having a largest intensity value within a wavelength range of 700 nm or more and less than 1000 nm. Furthermore, the phosphors also preferably are made of only the red phosphor and the near-infrared phosphor. In this way, primary light 3B emitted by the solid-state light emitting element 3 can be easily wavelength-converted into red and near-infrared optical components, and this is advantageous for obtaining the red and near-infrared optical components required for the inspection light 11.

EXAMPLES

The present embodiment will be described in more detail below using an example, but the present embodiment is not limited to this example.

[Manufacturing of Light Source]

A first wavelength conversion-type light emitting element including a solid-state light emitting element 3 which emits primary light 3B that is blue light (peak wavelength: 400 to 455 nm) and a first wavelength converter 1A was first manufactured.

For the solid-state light emitting element 3, a blue LED chip was used, and for the blue LED chip, product number: LE B P2MQ manufactured by OSRAM Opto Semiconductors GmbH was used. The first wavelength converter 1A was a resin fluorescent film containing $Y_3Al_2(AlO_4)_3:Ce^{3+}$ phosphor (YAG phosphor) and $(Sr, Ca)AlSiN_3:Eu^{2+}$ phosphor (SCASN phosphor). The first wavelength converter 1A and the first wavelength conversion-type light emitting element were manufactured as follows.

First, a YAG phosphor and an SCASN phosphor were prepared as phosphor powders. A YAG phosphor used was manufactured by TOKYO KAGAKU KENKYUSHO CO., LTD. and had a median particle size $D_{50}$ of about 24 μm. The YAG phosphor had a fluorescence peak around 540 nm and emitted yellow-green light. A SCASN phosphor used was manufactured by Mitsubishi Chemical Corporation and had a median particle size $D_{50}$ of about 14 μm. This SCASN phosphor had a fluorescence peak around 625 nm and emitted red light. In addition, a two-liquid mixing type thermosetting silicone resin (manufactured by Shin-Etsu Chemical Co., Ltd., product name: KER-2500A/B) was prepared as a sealant for the phosphor powders.

Next, the YAG phosphor (2.352 g) and the SCASN phosphor (0.504 g) were mixed with the silicone resin (agent 'A' 0.75 g, agent 'B' 0.75 g) and further defoamed using a stirring and defoaming device. Here, the stirring and defoaming device used was manufactured by THINKY CORPORATION, product name. Awatori Rentaro (registered trademark), model: ARE-310. The rotation speed of the stirring and defoaming device was set to about 2,000 rpm and the process was performed for 3 minutes. Thus, a phosphor paste made of the YAG phosphor, the SCASN phosphor, and the silicone resin was manufactured.

The phosphor paste thus obtained was dropped using a dispenser (model: ML-5000 XII, manufactured by Musashi Engineering, Inc.) into a frame having a height of about 210 μm provided around the blue LED chip. The phosphor paste was then heated in air at 150° C. for 2 hours to be cured. In this way, a resin fluorescent film having a thickness of about 200 μm was formed on the main light extraction surface of the blue LED to form the first wavelength converter 1A (length 5 mm, width 5 mm, thickness about 200 μm) and the first wavelength conversion-type light emitting element.

Next, a second wavelength conversion-type light emitting element composed of the solid-state light emitting element 3 and the second wavelength converter 2A was manufactured. For the solid-state light emitting element 3, a blue LED chip was used as in the first wavelength conversion-type light emitting element. The second wavelength converter 2A was a resin fluorescent film that contained a phosphor having a fluorescence peak at around 750 nm and containing mainly a composite metal oxide activated with $Cr^{3+}$. Note that the phosphor is a $(Gd, La)_3Ga_2(GaO_4)_3:Cr^{3+}$ phosphor (GLGG phosphor) expressed by the composition formula of $(Gd_{0.95}La_{0.05})_3(Ga_{0.97}Cr_{0.03})_2(GaO_4)_3$ and has a garnet-type crystal structure.

The GLGG phosphor was prepared through an orthodox solid phase reaction using the following compound powders as the main raw materials.

Gadolinium oxide $(Gd_2O_3)$: purity 3N, manufactured by NIPPON YTTRIUM CO., LTD.

Lanthanum hydroxide (La(OH)$_3$): purity 3N, manufactured by Shin-Etsu Chemical Co., Ltd.

Gallium oxide (Ga$_2$O$_3$): purity 4N, manufactured by Nippon Rare Metal, Inc.

Chromium oxide (Cr$_2$O$_3$): purity 3N, manufactured by Kojundo Chemical Lab. Co., Ltd.

Specifically, the above raw materials were first weighed so as to produce a compound having a stoichiometric composition (Gd$_{0.95}$La$_{0.05}$)$_3$(Ga$_{0.97}$Cr$_{0.03}$)$_2$(GaO$_4$)$_3$ through chemical reaction. Table 1 shows the weighed values of the raw materials.

TABLE 1

| General formula | Raw material (g) | | | |
|---|---|---|---|---|
| | Gd$_2$O$_3$ | La(OH)$_3$ | Ga$_2$O$_3$ | Cr$_2$O$_3$ |
| (Gd$_{0.95}$La$_{0.05}$)$_3$(Ga$_{0.97}$Cr$_{0.03}$)$_2$Ga$_3$O$_{12}$ | 10.213 | 0.563 | 9.154 | 0.090 |

Next, 20 g of the weighed raw materials was put into an alumina pot mill (capacity 250 ml) with alumina balls (diameter φ3 mm, total 200 g) and 60 ml of ethanol. The raw material was then wet-mixed using a planetary ball mill (manufactured by Fritsch Japan Co., Ltd, product number P-5) by rotating the pot mill at a rotation speed of 150 rpm for 30 minutes.

The alumina balls were then removed using a sieve to obtain a slurry-like mixed raw material of raw materials and ethanol. The mixed raw material was then dried at 125° C. using a dryer. The dried mixed raw material was then lightly mixed using a mortar and pestle to make a phosphor raw material.

Next, the phosphor raw material was put in an alumina calcining vessel (material SSA-H, size B3, with lid) and calcined for 2 hours in air at 1500° C. using a box-shaped electric furnace. Note that the temperature rise and fall rate during calcination was set at 300° C./h.

The obtained calcined product was hand-crushed using an alumina mortar and pestle, and coarse particles were removed by passing it through a nylon mesh (95 μm mesh opening) to obtain a powdery GLGG phosphor.

Although the data is omitted, the crystal composition of the obtained GLGG phosphor was evaluated using an X-ray diffractometer (desktop X-ray diffractometer, MiniFlex, manufactured by Rigaku Corporation), and it was mostly a garnet compound in a single crystal phase. Furthermore, the particle shape and size of the GLGG phosphor were evaluated using an electron microscope (desktop microscope Miniscope (registered trademark) TM4000, manufactured by Hitachi High-Technologies Corporation). As a result, the particle shape of the GLGG phosphor was a monodispersed particle shape, the particle shape was a shape that can be regarded as originating from garnet crystals, and the major particle size was around 15 μm.

Then, fluorescence properties of the GLGG phosphor were evaluated under irradiation with blue light at a wavelength of 450 nm using an absolute PL quantum yield spectrometer (C9920-02, manufactured by HAMAMATSU PHOTONICS K.K.). As a result, the fluorescence peak wavelength was 747 nm, the internal quantum efficiency (IQE) was 92%, and the light absorption rate (Abs.) of blue light was 57%. As a result of evaluation under irradiation with red light having a wavelength of 628 nm, the fluorescence peak wavelength was 746 nm, the internal quantum efficiency (IQE) was 93%, and the light absorption rate (Abs.) of red light was 45%.

Using the GLGG phosphor (4.57 g) thus manufactured, the second wavelength converter 2A (length 5 mm, width 5 mm, thickness 310 μm) and the second wavelength conversion-type light emitting element were manufactured by the same procedure as for the first wavelength converter 1A.

Then, the light source 10 as illustrated in FIG. 5 was manufactured using a first wavelength conversion-type light emitting element composed of a blue LED and the first wavelength converter 1A, and using a second wavelength conversion-type light emitting element composed of a blue LED and the second wavelength converter 2A.

[Evaluation]

The light source obtained was evaluated for emission properties. First, when a current of 500 mA was applied to the blue LED chip of the first wavelength conversion-type light emitting element, blue light as primary light 3B was emitted from the blue LED chip. Furthermore, part of the light was converted by the first wavelength converter 1A into visible light (orange light through additive mixture of a weak green optical component and a strong red optical component) as the first wavelength-converted light 1B. Then, first mixed light made of blue light as the primary light 3B and visible light as the first wavelength-converted light 1B was emitted from the first wavelength conversion-type light emitting element. Note that partly because the output ratio of the blue optical component was small, the appearance of the mixed light was substantially orange light, and the light was a tone that could not be considered to be white light.

Next, when a current of 500 mA was applied to the blue LED chip of the second wavelength conversion-type light emitting element, blue light as primary light 3B was emitted from the blue LED chip. Furthermore, part of the light was converted by the second wavelength converter 2A into near-infrared light as second wavelength-converted light 2B. Then, second mixed light (purple light) including blue light as the primary light 3B and near-infrared light as the second wavelength-converted light 2B was emitted from the second wavelength conversion-type light emitting element.

Then, as the first mixed light and the second mixed light were further mixed, mixed light made of the primary light 3B, the first wavelength-converted light 1B, and the second wavelength-converted light 2B was emitted as output light (inspection light 11). Note that the spectral distribution illustrated in FIG. 3 is the spectral distribution of output light emitted from the light source of the present example.

As can be seen from FIG. 3, the spectral distribution of the inspection light 11 has two maximum values 11A, 11B, which are derived from the fluorescent component emitted by the phosphors. In the two maximum values 11A, 11B, the maximum value 11A at which the spectral intensity is larger is at the wavelength of 618 nm. When the spectral intensity at the maximum value 11A is assumed to be 100%, the largest value of the spectral intensity in the wavelength range longer than 750 nm is 61% of the spectral intensity for the wavelength for the maximum value 11A. Note that "61%" is the value at the wavelength of 750 nm. The spectral intensity within the wavelength range of 500 nm or more and 550 nm or less was 16% of the spectral intensity at the wavelength for the maximum value 11A. Note that "16%" is the value at the wavelength of 550 nm.

In addition, for the spectral intensity within the wavelength range of 550 nm or more and 850 nm or less, the amount of change with respect to wavelength had a largest value of 4.6% per 1 nm wavelength.

Figure 6:
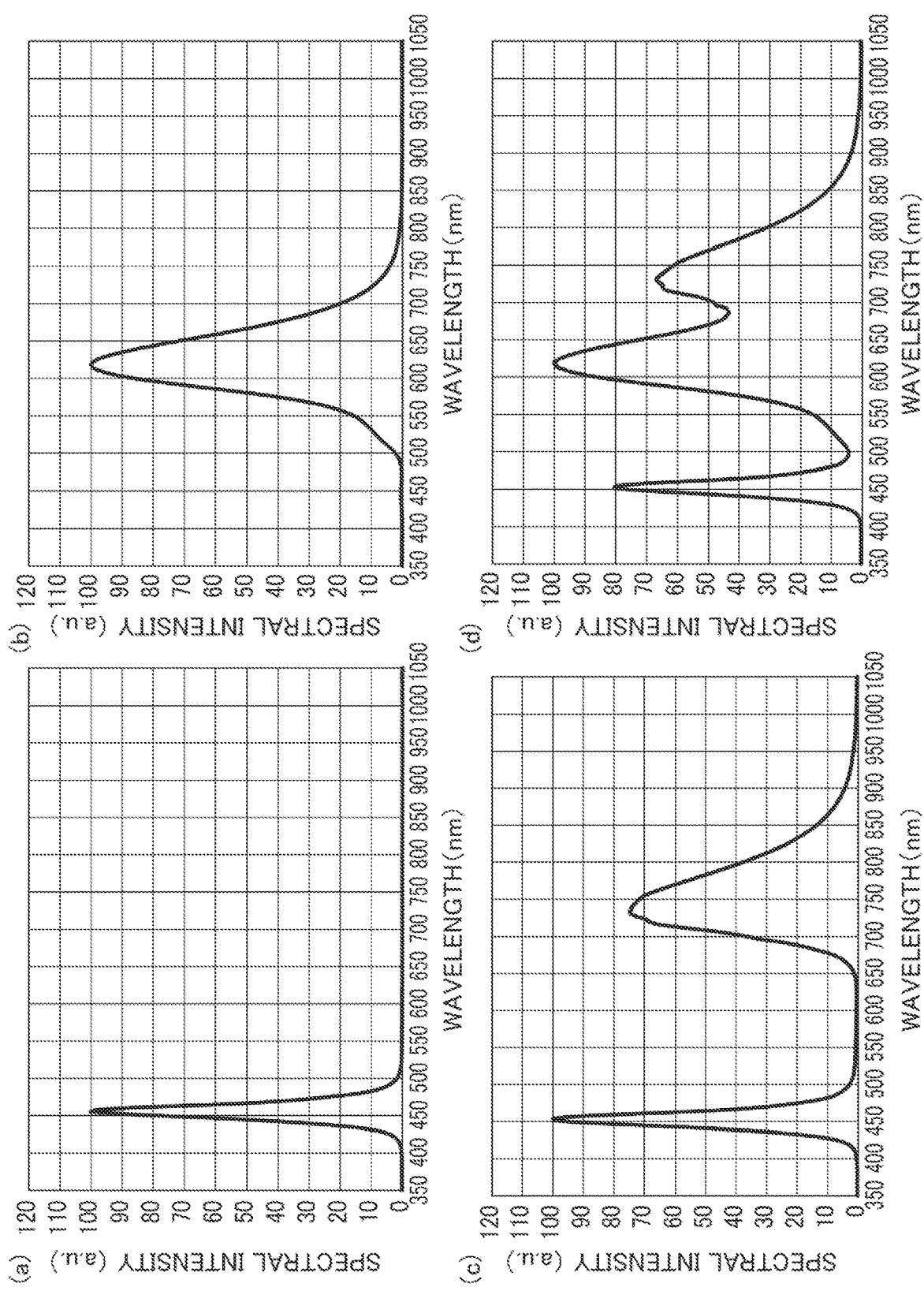
FIG. 6(a) is a graph illustrating a spectral distribution of primary light emitted by a blue LED chip in a practical example.
FIG. 6(b) is a graph illustrating a spectral distribution of mixed light of primary light transmitted through a first wavelength converter and of first wavelength-converted light in the practical example.
FIG. 6(c) is a graph illustrating a spectral distribution of mixed light of primary light transmitted through a second wavelength converter and of second wavelength-converted light in the practical example.
FIG. 6(d) is a graph illustrating a spectral distribution of inspection light obtained by further mixing the mixed light of FIG. 6(b) and the mixed light of FIG. 6(c) in the practical example.

For reference, FIG. 6(a) illustrates the spectral distribution of the primary light 3B emitted by the blue LED chip. FIG. 6(b) illustrates the spectral distribution of mixed light of the primary light 3B transmitted through the first wavelength converter 1A and the first wavelength-converted light 1B. FIG. 6(c) illustrates the spectral distribution of mixed light of the primary light 3B transmitted through the second wavelength converter 2A and the second wavelength-converted light 2B. FIG. 6(d) illustrates the spectral distribution of the inspection light 11 obtained by further mixing the mixed light of FIG. 6(b) and the mixed light of FIG. 6(c).

As can be seen from FIG. 6(a), primary light 3B was unimodal blue light having a fluorescence peak at the wavelength of 455 nm, and having a half-width of about 22 nm (15 nm or more and less than 30 nm).

As can be seen from FIG. 6(b), the mixed light of the primary light 3B transmitted through the first wavelength converter 1A and first wavelength-converted light 1B contains optical components of the primary light 3B having a weak intensity and the first wavelength-converted light 1B. The mixed light was orange-red light, but the correlated color temperature could not be calculated, the duv index indicating deviation from blackbody radiation could also not be calculated, and the general color rendering index Ra could also not be calculated. Note that the mixed light had a chromaticity of (x,y)=(0.594, 0.398) in the CIE chromaticity coordinates. In addition, the optical components of the first wavelength-converted light 1B were unimodal broad optical components having a peak at a wavelength of 618 nm and having optical components over a wide wavelength range from at least 500 nm to 800 nm.

As can be seen from FIG. 6(c), the mixed light of the primary light 3B transmitted through the second wavelength converter 2A and the second wavelength-converted light 2B contains optical components of the primary light 3B and the second wavelength-converted light 2B. The mixed light was substantially blue light, but the correlated color temperature could not be calculated, the duv could also not be calculated, and the general color rendering index Ra could also not be calculated. Note that the mixed light had a chromaticity of (x,y)=(0.159, 0.043) in the CIE chromaticity coordinates. In addition, the optical components of the second wavelength-converted light 2B were unimodal broad optical components having a peak at a wavelength of 733 nm and having optical components over a wide wavelength range of at least 650 nm and 950 nm or less.

As can be seen from FIG. 6(d), the inspection light 11 contained optical components of the primary light 3B, the first wavelength-converted light 1B, and the second wavelength-converted light 2B, and was slightly whitish red-purple light. Also, the inspection light 11 had a correlated color temperature of 1,736 K, a duv of −49.6, a general color rendering index Ra of 60, and a chromaticity of (x,y)=(0.456, 0.286) in the CIE chromaticity coordinates. The optical components of the inspection light 11 were multimodal optical components having peaks at wavelengths of 453 nm, 618 nm, and 732 nm and having optical components over a wide wavelength range of at least 410 nm and 950 nm or less.

Note that the inspection light 11 was emitted on a blank sheet placed 20 cm ahead of the light source, and the light emitted on the blank sheet was visually confirmed. As a result, the emitted light was homogeneous within a range of at least φ20 cm.

Next, the inspection device illustrated in FIG. 2 was manufactured using the light source 10. The photodetector 20 was first placed directly above the inspection object 30 and further at a distance of about 20 cm from the inspection object 30. The photodetector 20 used was a hyperspectral camera (manufactured by XIMEA, model number: MQ022HG-IM-SM4X4-REDNIR). In addition, the light source 10 described above was placed obliquely upward at about 45 degrees from the inspection object 30 and further at a distance of about 20 cm from the inspection object 30. Thus, the inspection device of the present example was obtained.

In this inspection device, after the light source 10 is energized and turned on, the inspection object 30 is irradiated with the emitted inspection light 11, and state thereof is observed using a hyperspectral camera. Thus, the state and condition of the inspection object 30 can be inspected.

The inspection device of the present example outputs inspection light including intense visible light in which optical components are concentrated in the wavelength range near 600 nm and including deep red to near-infrared light in which optical components are concentrated in the wavelength range near 730 nm. Therefore, it is possible to simultaneously detect foreign matter having a large reflectance difference with the inspection object in the deep-red to near-infrared wavelength range and foreign matter similar to said foreign matter but having a small reflectance difference in the deep-red to near-infrared wavelength range. In addition, since the inspection object is irradiated with intense red light, even foreign matter having a relatively small reflectance difference in the red wavelength range with respect to the inspection object can be detected with high sensitivity.

Furthermore, the light source of the inspection device in the present example is excellent in electro-optical conversion efficiency because it converts the input power into light concentrated in the minimum optical components required for detection. Therefore, the inspection device in the present example is advantageous in reducing power consumption and resource conservation, as well as in making it compact and high power.

Although the present embodiment has been described above, the present embodiment is not limited to these descriptions, and various modifications are possible within the scope of the gist according to the present embodiment.

The entire contents of Japanese Patent Application No. 2021-026793 (filed Feb. 22, 2021) are incorporated herein by reference.

INDUSTRIAL APPLICABILITY

The present disclosure makes it possible to provide an inspection device and an inspection method capable of detecting foreign matter whose light absorption property and light reflection property in the near-infrared region are similar to those of an inspection object and further being advantageous for reducing the size and increasing the power of a light source.

REFERENCE SIGNS LIST

3 Solid-state light emitting element
10 Light source
11 Inspection light
11A, 11B Maximum value
12 Reflected light
20 Photodetector
30 Inspection object
100 Inspection device

The invention claimed is:

1. An inspection device comprising:
a light source including a phosphor configured to irradiate an inspection object with inspection light; and
a photodetector configured to detect reflected light of the inspection light, wherein
 a spectral distribution of the inspection light has at least one local maximum spectral intensity value derived from fluorescence emitted by the phosphor,
 there are two local maximum spectral intensity values within a wavelength range of 500 nm or more and less than or equal to 1000 nm,
 a maximum spectral intensity value is within a wavelength range of 600 nm or more and less than or equal to 750 nm,
 when a spectral intensity value Pmax equals the maximum spectral intensity value, a largest value of the spectral intensity in a wavelength range longer than 750 nm is within a range of 20% or more of Pmax and less than or equal to 100% of Pmax, and
 the spectral intensity value within a wavelength range of 500 nm or more and less than or equal to 550 nm is less than 20% of Pmax.

2. The inspection device according to claim 1, wherein the first local maximum spectral intensity value derived from the fluorescence emitted by the phosphor has a greatest spectral intensity value in the spectral distribution.

3. The inspection device according to claim 1, wherein the spectral intensity within a wavelength range of 550 nm or more and less than or equal to 850 nm, an amount of spectral intensity change with respect to wavelength is less than 5% per 1 nm wavelength.

4. The inspection device according to claim 1, wherein the light source is a combination of a solid-state light emitting element and the phosphor.

5. The inspection device according to claim 4, wherein the solid-state light emitting element emits light having a greatest spectral intensity value within a wavelength range of 440 nm or more and less than or equal to 480 nm.

6. The inspection device according to claim 1, wherein the phosphor comprises a red phosphor that emits red light having a greatest spectral intensity value within a wavelength range of 600 nm or more and less than or equal to 660 nm, and a near-infrared phosphor that emits near-infrared light having a greatest spectral intensity value within a wavelength range of 700 nm or more and less than or equal to 1000 nm.

7. The inspection device according to claim 6, wherein the red phosphor is a phosphor made from a metal composite nitride or metal composite oxynitride activated with $Eu^{2+}$, and
 the near-infrared phosphor is a phosphor made from a metal composite oxide activated with $Cr^{3+}$.

8. The inspection device according to claim 6, wherein the phosphor consists of the red phosphor and the near-infrared phosphor.

9. The inspection device according to claim 1, wherein the inspection object is food.

10. The inspection device according to claim 1, wherein the inspection device is configured to detect foreign matter within the inspection object.

11. The inspection device according to claim 10, wherein the foreign matter is hair.

12. The inspection device according to claim 1, wherein a greatest value of the spectral intensity in the wavelength range longer than 750 nm is between 30% or more and less than or equal to 80% of Pmax.

13. The inspection device according to claim 1, wherein a greatest value of the spectral intensity in the wavelength range longer than 750 nm is between 50% or more and less than or equal to 70% of Pmax.

14. The inspection device according to claim 1, wherein the inspection light contains red light having the maximum spectral intensity value in the wavelength range of 600 nm or more and less than or equal to 750 nm and near-infrared light having the wavelength range longer than 750 nm, and the spectral intensity of the red light is greater than that of the near-infrared light.

15. An inspection method, comprising:
 irradiating an inspection object with inspection light emitted by a light source including a phosphor; and
 detecting, using a photodetector, reflected light of the inspection light reflected by the inspection object, wherein
  a spectral distribution of the inspection light has at least one local maximum spectral intensity value derived from fluorescence emitted by the phosphor,
  there are two local maximum spectral intensity values within a wavelength range of 500 nm or more and less than or equal to 1000 nm,
  a maximum spectral intensity value is within a wavelength range of 600 nm or more and less than or equal to 750 nm, and
  when a spectral intensity value Pmax equals the maximum spectral intensity value, a largest value of the spectral intensity in a wavelength range longer than 750 nm is within a range of 20% or more of Pmax and less than or equal to 100% of Pmax, and
  the spectral intensity value within a wavelength range of 500 nm or more and less than or equal to 550 nm is less than 20% of Pmax.

\* \* \* \* \*